United States Patent
Laskin et al.

(10) Patent No.: US 7,105,511 B2
(45) Date of Patent: Sep. 12, 2006

(54) FLUORESCENT FUSED-RING TRIAZOLES THAT INHIBIT CELL PROLIFERATION AND USES THEREOF

(75) Inventors: Jeffrey D. Laskin, Piscataway, NJ (US); Ned Heindel, Easton, PA (US); Diane Heck, Rumson, NJ (US); Anna Marie Vetrano, North Brunswick, NJ (US); Christophe Guillon, Bethlehem, PA (US); Peter DeMatteo, Allentown, PA (US)

(73) Assignees: University of Medicine and Dentistry of New Jersey, New Brunswick, NJ (US); Rutgers, the State University, New Brunswick, NJ (US); Lehigh University, Bethlehem, PA (US)

( * ) Notice: Subject to any disclaimer, the term of this patent is extended or adjusted under 35 U.S.C. 154(b) by 163 days.

(21) Appl. No.: 10/922,300

(22) Filed: Aug. 19, 2004

(65) Prior Publication Data

US 2006/0040926 A1    Feb. 23, 2006

(51) Int. Cl.
  *C07D 513/04*   (2006.01)
  *A61K 31/542*   (2006.01)
  *A61P 35/00*    (2006.01)
(52) U.S. Cl. ..................... 514/222.8; 544/10
(58) Field of Classification Search ................. 544/10; 514/222.8
  See application file for complete search history.

(56) References Cited

OTHER PUBLICATIONS

Angibaud et al., "4-Methyl-1,2,4-triazol-3-yl Heterocycle as an Alternative to the 1-Methylimidazol-5-yl Moeity in the Farnesyltransferase Inhibitor ZARNESTRA", Bioorganic & Medicinal Chemistry Letters 2003 13:4361-4364.
Catarzi et al., "Synthesis and Biological Evaluation of Analogues of 7-Chloro-4,5-dihydro-4-oxo-8-(1,2,4-triazol-4-yl)-1,2,4-triazolo [1,5-a] quinoxaline-2-carboxylic Acid (TQX-173) as Novel Selective AMPA Receptor Antagonists", J. Med. Chem. 2004 47:262-272.
Demirbas et al., "Synthesis of 3-Alkyl (Aryl)-4-alkylidenamino-4,5-dihydro-1H-1,2,4-triazol-5-ones and 3-Alkyl-4-alkylamino-4,5-dihydro-1H-1,2,4-triazol-5-ones as Antitumor Agents", Bioorganic & Medicinal Chemistry 2002 10:3717-3723.
Ikeda et al., "Synthesis of a novel histidine analogue and its efficient incorporation into a protein *in vivo*", Protein Engineering 2003 16(9):699-706.
Torurirte et al., "Synthesis of 3'-deoxy-3'- [4-(pyrimidin-1-yl)methyl-1,2,3-triazol-1-yl] thymidine via 1,3-dipolar cycloaddition", Nucleosides Nucleotides Nucleic Acids 2003 22(11):1985-1993.
Pomarnacka et al., "Synthesis of 1- (6-chloro-1,1-dioxo-1,4,2-benzodithiazin-3-yl) semi-carbazides and their transformation into 4-chloro-2-mercapto-*N*- (4,5-dihydro-5-oxo-4-phenyl-1*H*-1,2,4-triazol-3-yl)benzenesulfonamides as potential anticancer and anti-HIV agents", Il Farmaco 2003 58:423-429.
Reid et al., "Improved Syntheses of 5-Substituted-4-amino-3-mercapto-(4*H*)-1,2,4-triazoles", J. Heterocyclic Chem. 1976 13:925-926.
Tominaga et al., "Early Phase II Study of the New Aromatase Inhibitor YM511 in Postmenopausal Patients with Breast Cancer. Difficulty in Clinical Dose Recommendation Based on Preclinical and Phase I Findings", Anticancer Research 2003 23:3533-3542.
Weier et al., "FISH in cancer diagnosis and prognostication:from cause to course of disease", Expert Rev. Mol. Diagn. 2002 2(2):109-119.
Xu et al., "Design and Synthesis of a Potent and Selective Triazolone-Based Peroxisome Proliferator-Activated Receptor α Agonist", J. Med. Chem. 2003 46:5121-5124.
Yurkow et al., "Mechanism of action of psoralens:isobologram analysis reveals that ultraviolet light potentiation of psoralen action is not additive but synergistic", Cancer Chemother Pharmacol 1991 27:315-319.

*Primary Examiner*—Kahsay Habte
(74) *Attorney, Agent, or Firm*—Licata & Tyrrell P.C.

(57) ABSTRACT

Fused-ring triazole compounds which inhibit proliferation of cells and exhibit a unique and intense fluorescence are provided. Also provided are methods for synthesizing these compounds and methods for using these compounds to inhibit cell proliferation and infection and to label and fluorescently detect selected molecules.

8 Claims, No Drawings

FLUORESCENT FUSED-RING TRIAZOLES THAT INHIBIT CELL PROLIFERATION AND USES THEREOF

This invention was supported in part by funds from the U.S. government (NIEHS #ES06897) and the U.S. government may therefore have certain rights in the invention.

FIELD OF THE INVENTION

The present invention relates to a new class of fused-ring triazoles and methods for synthesis of these compounds. The present invention also relates to compositions comprising these fused-ring triazoles and methods for use of these compositions as anti-proliferative agents, anti-estrogenic agents, anti-microbial agents and/or anti-viral agents. These fused-ring triazoles have been found to be intensely fluorescent when excited at selected wavelengths. The fluorescent properties of these compounds are useful in tracking these compounds, for example in pharmacokinetic studies of these therapeutic agents. Their fluorescent properties also make them useful as fluorescent probes.

BACKGROUND OF THE INVENTION

The 1,2,4-triazole moiety is an important and versatile pharmacophore often found as a structural unit in diverse pharmaceutical classes. Antifungal imidazoles and indeed almost any important pharmaceutical, in which a five-membered nitrogen heterocyclic residue is incorporated, can be synthesized with a 1,2,4-triazole as a surrogate for that imidazole with retention of the model compound's original pharmacologic activity (Angibaud et al. *Bioorg. Med. Chem. Lett.* 2003 13:4361–4364). Biological pathways requiring histidine can be manipulated into accepting and incorporating the triazole analogue into the resulting protein (Ikeda et al. *Protein Eng.* 2003 16:699–706). Furthermore, the 1,2,4-triazole has been observed as a bioisostere for a phenyl ring in the PPARα agonists being explored as lipid-lowering drugs (Xu et al. *J. Med. Chem.* 2003 46:5121–5124).

A functionalized 1,2,4-triazole attached to a benzonitrile moiety is in clinical trials for breast cancer and is showing significant activity (Tominaga, T. and Suzuki, T. *Anticancer Res.* 2003 4:3533–3542). 1,2,4-Triazoles with alkylamino side chains were inhibitory against a host of malignant cell lines (Demirbas et al. *Bioorg. Med. Chem.* 2002 10:3717–3723). Dimers of 1,2,4-triazol-5-thiols were active against seven cancer types (Holla et al. *Eur. J. Med. Chem.* 2002 37:511–517). Both antitumor and anti-HIV activity were observed in triazoles fused to benzene sulfonamides (Pomarnacka E, Kozlarska-Kedra I, *Farmaco* 2003 58:423–429).

Fused ring systems in which the 1,2,4-triazole nucleus is the core of a larger heterocyclic pharmaceutical are showing considerable therapeutic promise. Catarzi reported that a triazole-quinoxaline class was potentially useful in neuro-protection (treatment and prevention of acute and chronic neurological disorders) (Catarzi et al. *J. Med. Chem.* 2004 47:262–272). Tourirte found modest inhibition of the replication of HIV by triazole-pyrimidines (Tourirte et al. *Nucleosides Nucleotide Nucleic Acids.* 2003 22:1985–1993).

Thus, the triazole nucleus is used widely in drug design and development.

SUMMARY OF THE INVENTION

A unique family of fused ring triazoles referred to herein as 3-R-7-(phenylmethylene)-s-triazolo[3,4-b][1,3,4]-thiadiazines has now been synthesized. This new class of fluorescent fused triazoles is useful as fluorescent probes and in the treatment of proliferative disorders and as anti-estrogenic, antimicrobial and antiviral agents.

Accordingly, an object of the present invention is to provide a compound of Formula II:

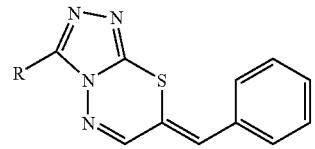

wherein R is selected from the group consisting of a furyl group, a thienyl group, a pyridyl group, an alkyl group, and an aryl or arylalkyl group. Preferably R is an aryl or arylalkyl group selected from the group consisting of 1-(2-phenyl)-ethyl, 3-methoxyphenyl, 4-trifluoromethylphenyl and 4-fluorophenyl, or a pyridyl group selected from the group consisting of 2-pyridyl, 3-pyridyl, and 4-pyridyl.

Another object of the present invention is to provide methods for synthesizing a compound of Formula II.

In one embodiment, the method of synthesis comprises a single step wherein α-bromocinnamaldehyde is added to a solution comprising a mercaptoaminotriazole and a tertiary amine, and a compound of Formula II precipitates therefrom.

In another embodiment, the method of synthesis comprises a two-step process wherein a bromocinnamyl imine is derived from the condensation of a mercaptoaminotriazole with an aldehyde, preferably α-bromocinnamaldehyde. The bromocinnamyl imine is then converted to a compound of Formula II by treatment at reflux with a tertiary amine.

Another object of the present invention is to provide a method for inhibiting cell proliferation which comprises administering to the cell a compound of Formula II.

Another object of the present invention is to provide a pharmaceutical composition comprising a compound of Formula II and a pharmaceutically acceptable vehicle.

Another object of the present invention is to provide a method for treating a proliferative disorder which comprises administering to a subject suffering from a proliferative disorder a pharmaceutical composition comprising a compound of Formula II and a pharmaceutically acceptable vehicle.

Another object of the present invention is to provide a method for inhibiting estrogen-mediated growth of cancer cells such as estrogen-dependent breast cancer cells which comprises administering to a subject suffering and estrogen-mediated cancer a pharmaceutical composition comprising a compound of Formula II and a pharmaceutically acceptable vehicle.

Another object of the present invention is to provide a method for treating a viral or microbial infection in a subject which comprises administering to a subject suffering from a microbial or viral infection a pharmaceutical composition comprising a compound of Formula II and a pharmaceutically acceptable vehicle.

Another object of the present invention is to provide a disinfectant or antiseptic agent comprising a compound of Formula II.

Another object of the present invention is to provide a fluorescent probe comprising a probe molecule fluorescently labeled with a compound of Formula II.

Yet another object of the present invention is to provide a method for fluorescently tagging a molecule of interest such as a selected protein or nucleic acid sequence using a fluorescent probe comprising a compound of Formula II.

DETAILED DESCRIPTION OF THE INVENTION

The present invention provides a novel class of fused ring triazole compounds represented by the following Formula II:

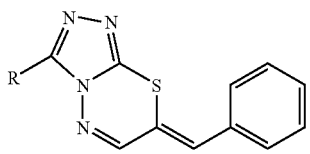

wherein R is selected from the group consisting of a furyl group, a thienyl group, a pyridyl group, an alkyl group, and an aryl or arylalkyl group. Preferably R is an aryl or arylalkyl group selected from the group consisting of 1-(2-phenyl)-ethyl, 3-methoxyphenyl, 4-trifluoromethylphenyl and 4-fluorophenyl, or a pyridyl group selected from the group consisting of 2-pyridyl, 3-pyridyl, and 4-pyridyl. This class of fused ring triazole compounds of the present invention is also referred to herein as 3-R-7-(phenylmethylene)-s-triazolo[3,4-b][1,3,4]-thiadiazines.

Also provided in the present invention are methods for synthesizing 3-R-7-(phenylmethylene)-s-triazolo [3,4-b][1,3,4]-thiadiazines of Formula II.

In one embodiment, these compounds are synthesized by a single-step process for preparation. The general scheme for this one-step preparation of a 3-R-7-(phenylmethylene)-s-triazolo [3,4-b][1,3,4]-thiadiazine is depicted in Scheme I:

Scheme I:

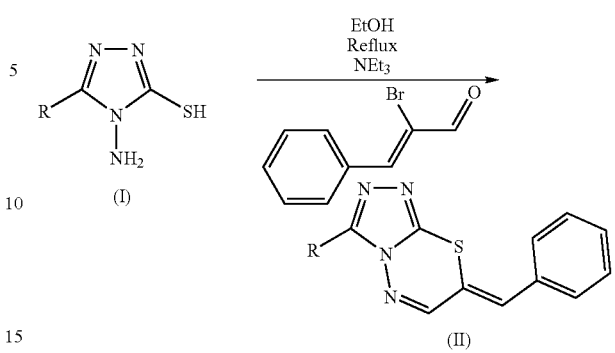

As shown in Scheme I, in this one-step synthesis, a solution of a mercaptoaminotriazole of Formula I, wherein R is selected from the group consisting of 2-pyridyl, 3-pyridyl, and 4-pyridyl, is prepared by refluxing with a tertiary amine such as triethylamine or pyridine in a solvent such as anhydrous ethanol or dioxane. An aldehyde, preferably an α-halocinnamaldehyde such as iodo-, bromo- or chloro-cinnamaldehyde, is then added to the solution and the resulting mixture is refluxed for several hours until a precipitate of the 3-R-7-(phenylmethylene)-s-triazolo [3,4-b][1,3,4]-thiadiazine forms.

This one-step synthetic method is particularly useful for synthesis of compounds of the present invention wherein R contains a basic moiety such as the nitrogen of a pyridyl or quinolinyl functionality. Yields ranging from about 50 to about 75% are generally achieved using this method. This one step-synthesis can also be applied to any mercaptoaminotriazole of Formula I wherein R is selected from the group consisting of a furyl group, a thienyl group, an alkyl group, or an aryl or arylalkyl group such as 1-(2-phenyl)-ethyl, 3-methoxyphenyl, 4-trifluoromethylphenyl or 4-fluorophenyl as long as an equivalent amount of a tertiary amine, such as triethylamine, is also used.

In another embodiment, compounds of the present invention are synthesized by a two-step process. The general scheme for this two-step preparation of a 3-R-7-(phenylmethylene)-s-triazolo[3,4-b][1,3,4]-thiadiazine is depicted in Scheme II:

Scheme II:

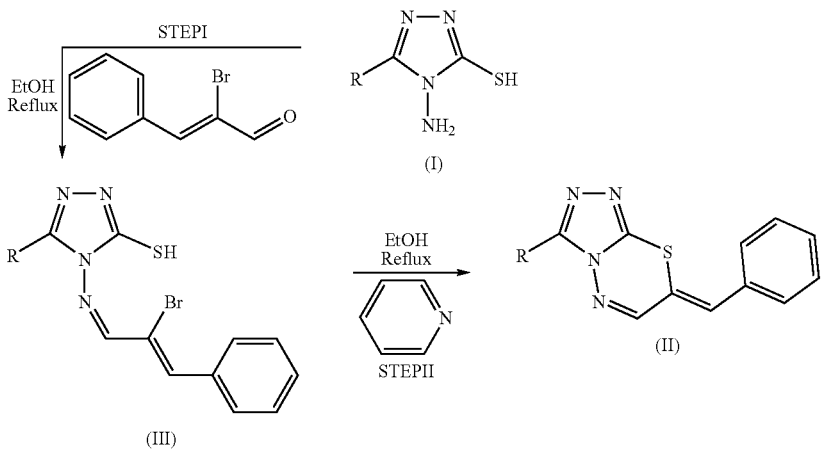

In step I, a bromocinnamyl imine is derived from the condensation of a mercaptoaminotriazole of Formula I with an aldehyde, preferably α-bromocinnamaldehyde, in accordance with procedures for preparation of 4-amino-3-mercapto-1,2,4-triazoles as set forth in WO 00/10564, which is herein incorporated by reference in its entirety. The resulting intermediate of bromocinnamyl imine (depicted in Formula III) has been isolated and characterized in >60% yields. These imines can be converted (step II) by treatment at reflux with an equivalent amount of a tertiary amine such as triethylamine or pyridine, in a solvent, preferably ethanol, to a 3-R-7-(phenylmethylene)-s-triazolo[3,4-b][1,3,4]-thiadiazine of Formula II with completion of the reaction defined by the time at which no detectable residue of Formula III, as determined by thin layer chromatography, remains.

Exemplary triazole compounds of the present invention synthesized in accordance with the one-step and/or two-step processes described herein include, but are in no way limited to,

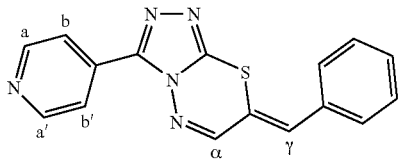

Compound IIa, viz., 3-(4-pyridyl)-7-(phenylmethylene)-s-triazolo [3,4-b][1,3,4]-thiadiazine, wherein R is 4-pyridyl

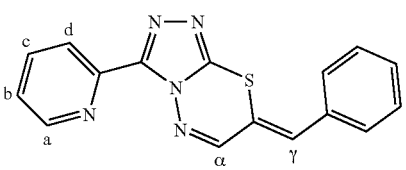

Compound IIb, viz., 3-(2-pyridyl)-7-(phenylmethylene)-s-triazolo [3,4-b][1,3,4]-thiadiazine, wherein R is 2-pyridyl,

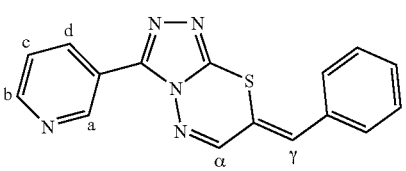

Compound IIc, viz., 3-(3-pyridyl)-7-(phenylmethylene)-s-triazolo [3,4-b][1,3,4]-thiadiazine, wherein R is 3-pyridyl,

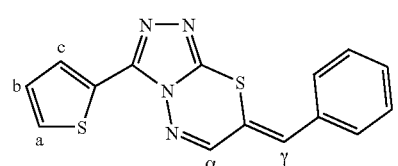

Compound IId, viz., 3-(2-thienyl)-7-(phenylmethylene)-s-triazolo [3,4-b][1,3,4]-thiadiazine, wherein R is 2-thienyl,

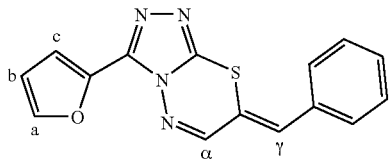

Compound IIe, viz., 3-(2-furyl)-7-(phenylmethylene)-s-triazolo [3,4-b][1,3,4]-thiadiazine, wherein R is 2-furyl,

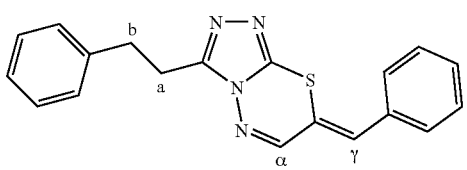

Compound IIf, viz., 3-(2-phenylethyl)-7-(phenylmethylene)-s-triazolo[3,4b][1,3,4]-thiadiazine, wherein R is 1-(2-phenyl)ethyl,

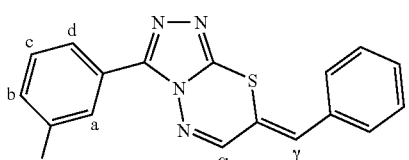

Compound IIg, viz., 3-(3-methoxyphenyl)-7-(phenylmethylene)-s-triazolo[3,4b][1,3,4]-thiadiazine, wherein R is 3-methoxyphenyl,

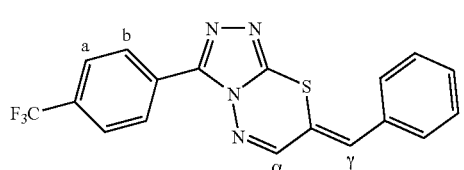

Compound IIh, viz., 3-(4-trifluoromethylphenyl)-7-(phenylmethylene)-s-triazolo[3,4b][1,3,4]-thiadiazine, wherein R is 4-trifluoromethylphenyl, and

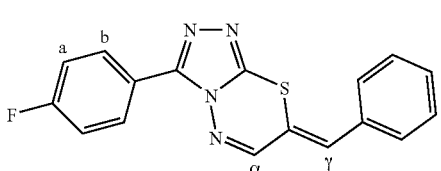

Compound IIi, viz., 3-(4-fluoromethylphenyl)-7-(phenylmethylene)-s-triazolo[3,4b][1,3,4]-thiadiazine, wherein R is 4-fluorophenyl.

The antiproliferative activity of compounds of the present invention was demonstrated in PAM 212 tumor cells.

Experiments were performed in accordance with the procedure described by Yurkow and Laskin (Cancer Chemother. Pharmacol. 1991 27:315–319). In these experiments, tumor cells were maintained in culture in growth medium consisting of Dulbecco's modified Eagle's medium (DMEM) supplemented with 10% fetal bovine. Tumor cells were plated at low density (5000 cells/well) in 6-well tissue culture dishes and allowed to adhere overnight. The medium was then replaced with phenol red-free DMEM supplemented with increasing concentrations of the compounds, with zero concentration of compound serving as the control. Six concentrations and a control were used for each inhibitor, and each concentration was tested in triplicate. After 5 days, cells were removed from the dishes and enumerated using a Coulter Counter (Coulter Electronics, Inc.). The controls and treated samples at each concentration were averaged. Data are presented as the percentage of control growth at each concentration of the compound, plus and minus the standard error. The $IC_{50}$ for growth inhibition was the concentration of each compound that inhibited growth by 50%. These are depicted in Table 1.

TABLE 1

Ability of Fused-Ring Triazoles to Inhibit Growth of Tumor Cells

| | IC50 of fused ring triazole | | |
|---|---|---|---|
| Cells type | IIa | IIb | IId |
| mouse PAM 212 keratinocytes | 10 μM | 18 μM | 18 μM |
| mouse B16 melanoma | 9 μM | 15 μM | 23 μM |
| human CX-1 colon cells | 17 μM | 30 μM | 20 μM |
| human HeLa cervical carcinoma | 4 μM | 9 μM | 28 μM |

IC50 = Concentration of each compound inhibiting growth of cell line by 50%.

Accordingly, the compounds of the present invention are useful as anti-proliferative agents, particularly in the inhibition of tumor cell growth.

Further, triazole compounds are commonly used as anti-estrogens for example, to suppress estrogen mediated cancers such as estrogen-dependent breast cancer development in humans.

Thus, it is expected that pharmaceutical compositions comprising a compound of the present invention will be useful in the treatment of cancer as well as other proliferative disorders or diseases including but not limited to, macular degeneration, psoriasis, arteriosclerosis and restenosis and as anti-estrogenic agents.

Further, the inhibitory properties of these agents are expected to be useful against bacterial and viral infections as well, thus making these compounds also useful as antimicrobial and/or antiviral agents.

Compounds of the present invention are expected to be useful as antiproliferative, anti-estrogenic, antiviral and/or antimicrobial agents in all animals, including but not limited to, humans, dogs, cats, birds, horses, cows, sheep, swine (pigs and hogs), and other farm animals, as well as rodents and other animals seen in zoos. Thus, while the activities of these new compounds are believed to be particularly useful for inhibiting tumor growth and infectious diseases in humans, use of these compounds for veterinary purposes is also clearly within the scope of the instant invention.

Therefore, another aspect of the present invention relates to pharmaceutical compositions comprising a compound of Formula II. Pharmaceutical compositions of the invention may further include excipients, stabilizers, emulsifiers, therapeutic adjuvants, diluents and the like, referred to herein in general as pharmaceutically acceptable vehicles. Sustained-released and time-release formulations are also encompassed within the present invention.

Suitable solid or liquid formulations for use in the present invention are, for example, granules, powders, coated tablets, microcapsules, suppositories, syrups, elixirs, suspensions, emulsions, drops or injectable solutions. Commonly used additives in protracted release preparations are excipients, disintegrates, binders, coating agents, swelling agents, glidants or lubricants, flavors, sweeteners or solubilizers. More specifically, frequently used additives are, for example, magnesium stearate, magnesium carbonate, titanium dioxide, lactose, mannitol and other sugars, talc, lactalbumin, gelatin, starch, cellulose and its derivatives, animal and vegetable oils, polyethylene glycols and solvents. Common solvents include sterile water and monohydric or polyhydric alcohols such as glycerol. Acceptable carriers, agents, excipients, stabilizers, diluents and the like for therapeutic use are well known in the pharmaceutical field, and are described, for example, in Remington's Pharmaceutical Sciences, Mack Publishing Co., ed. A. R. Gennaro (1985). If appropriate, the compound may be administered in the form of a physiologically acceptable salt, for example, an acid-addition salt. The pharmaceutical compositions are preferably produced and administered in dosage units, each unit containing as an active component an effective dose of at least one compound of the present invention and/or at least one of its physiologically acceptable salts. The effective dose to treat diseases such as those discussed above typically ranges from about 1 to about 100 mg/kg of body weight per day.

The pharmaceutical compositions according to the invention are suitable for use as anti-proliferative, antimicrobial and/or antiviral agents in a subject, particularly a human patient or subject, and comprise an effective amount of a fused triazole compound according to the present invention and a pharmaceutically acceptable vehicle, carrier or diluent.

Such compositions may be administered by various routes selected in accordance with the condition to be treated. Exemplary routes of administration include, but are not limited, intravenously, orally, intramuscularly, parenterally, topically, bucally, via inhalation, and rectally.

For intravenous infusion or intravenous bolus injection, or parenteral or intramuscular injection, the active ingredient is dissolved in a pharmaceutically acceptable vehicle such as saline or phosphate buffered saline.

For oral treatment, administration of the active ingredient may be, for example, in the form of tablets, capsules, powders, syrups, or solutions. For tablet preparation, the usual tablet adjuvants such as cornstarch, potato starch, talcum, magnesium stearate, gelatin, lactose, gums, or the like may be employed, but any other pharmaceutical tableting adjuvants may also be used, provided only that they are compatible with the active ingredient. In general, an oral dosage regimen will include about 5 mg to about 50 mg, preferably from about 5 to about 10 mg, per kg of body weight. Such administration and selection of dosage and unit dosage will of course have to be determined according to established medical principles and under the supervision of the physician in charge of the therapy involved.

For topical applications, solutions or ointments may be prepared and employed. These may be formulated with any one of a number of pharmaceutically acceptable carriers, as is well known in the art. Topical formulations comprise an effective amount of the active ingredient per unit area. Preferably, the topical formulation is in the form of a one percent solution, suspension or ointment and is applied on the skin at about 0.1 mL per square centimeter. The formulations may contain a suitable carrier such as ethanol or any of the pharmaceutically acceptable carriers described supra.

The antiviral and/or antimicrobial activities of these compounds also render them useful as disinfectants or aseptic agents. The triazole compounds of the present invention, as disinfectants or antiseptic agents, are suitable for various uses including, but not limited to, water purifying agents, sanitizers and bactericides for use, for example, in room temperature methods for sterilizing a surface medical instruments or devices. Further, these compounds can be used to sterilize biological and medical fluids including, but not limited to blood, cerebrospinal fluid, and fluid replacements. The compounds can also be used to sterilize tissues, prosthetic implants or chemical compositions prior to administration, implantations or insertion during various medical procedures. For example, in one nonlimiting embodiment, the compound can be used to sterilize oral tissues prior to invasive dental procedures. In an alternative nonlimiting embodiment, the compound can be used to sterilize a chemical composition prior to administration into, for example, the vaginal canal to prevent the transmission of sexually transmitted diseases. Disinfectants or antiseptic agents of the present invention comprise a solution or suspension of a compound of Formula II. Other components of the solution or suspension may include those ingredients routinely incorporated into disinfectants and/or antiseptic agents and well known to those skilled in the art. Examples of additional components which can be included in the disinfectants or antiseptic agents include, but are in no way limited to alcohols, oxidizing agents such as hydrogen or benzoyl peroxide, halogens such as chlorides or iodides, heavy metals and quaternary ammonium compounds.

The triazole compounds of the present invention also exhibit a unique and intense fluorescent spectrum. Characteristics of their fluorescence spectra are shown in Table 2.

TABLE 2

Characteristics of Fluorescence Spectra of Representative Fused Ring Triazoles

| Compound | Excitation peaks | Emission peak |
|---|---|---|
| IIa | 224 nm, 286 nm | 358 nm |
| IIb | 249 nm | 320 nm |

Excitation and emission spectra of a 10 micromolar solution of compounds IIa and IIb were determined using a Perkin-Elmer LS-5B Luminescence Spectrometer.

The fluorescent properties of these compounds are useful in tracking these compounds, for example in pharmacokinetic studies of these therapeutic agents. Their fluorescent properties also make them useful as fluorescent probes.

Accordingly, another aspect of the present invention relates to fluorescent probes comprising a compound of Formula II. Fluorescent probes are used extensively in cell and molecular biology and in clinical diagnosis to detect specific proteins and/or nucleic acid sequences such as DNA and RNA.

In one embodiment of the present invention, a fluorescent probe comprising a compound of Formula II is used to detect minute quantities of a selected protein or proteins or a nucleic acid sequence or sequences such as DNA and RNA in biological samples by covalently modifying the molecule of interest with the intensely fluorescent compound. Alternatively, a compound of Formula II can be attached or linked to a second agent, which directs binding of the probe to a selected molecule. Examples of second agents include, but are in no limited to, antibodies or other binding agent such as avidin, which can be used to detect selected molecules such as antigens. An additional example of a second agent is an agent that binds DNA, RNA or protein, for example, a dye that intercalates DNA and directs the fluorescent probe to a selected molecule such as a DNA, RNA or protein.

Fluorescence techniques are used increasingly in a variety of clinical assays.

For example, fluorescence techniques are used routinely in microscopy, whole animal imaging, fluorescence microplate readers and in flow cytometry in the detection of different types of cells of a tumor or in blood. The Fluorescence Activated Cell Sorter (FACS) was invented in the late 1960s by Bonner, Sweet, Hulett, Herzenberg, and others to do flow cytometry and cell sorting of viable cells and commercial machines were introduced by Becton Dickinson in the early 1970s. (Ehrenberg et al. Clin Chem. 2002 October;48(10):1819–27). Over the years, the number of measured FACS dimensions or parameters, as well as the speed of sorting, has been increased to where 12 fluorescent colors plus 2 scatter parameters can now be measured simultaneously. Flow cytometry via FACS thus has great utility as it allows for simultaneous staining and analysis, followed by sorting of cells from small samples of human blood cells. Analysis and sorting of multiple subpopulations of, for example, lymphocytes, by use of 8 to 12 colors can be performed. Alternatively, FACS and flow cytometry can be used in single cell sorting, for example, to clone and analyze hybridomas.

Fluorescence techniques are also used for chromosome analysis and/or molecular cytogenetics. The last 20 years have witnessed an astounding evolution of cytogenetic approaches to, for example cancer diagnosis and prognostication. Molecular techniques and, in particular, nonisotopically-labeled nucleic acid probes and fluorescence in situ hybridization (FISH)-based techniques have replaced the costly and potentially dangerous radioactive techniques used in research and the clinical detection of genetic alterations in tumor cells (Weier et al. Expert Rev Mol Diagn. 2002 March;2(2):109–19). Fluorescent DNA probes also enable the screening for very subtle chromosomal changes. Clinical laboratories now select from a growing number of FISH-based cytogenetic tests to support physician's diagnoses of the causes and the course of a disease. Depending on the specimen, state-of-the-art FISH techniques allow the localization and scoring of 10–24 different targets and overcome previous problems associated with target colocalization and detection system bandwidth. FISH-based analyses have been applied very successfully to the analysis of single cells and have demonstrated the existence of cell clones of different chromosomal make-up within human tumors. This information provides disease-specific information to the attending physician and should enable the design of patient-specific protocols for disease intervention.

Fluorescence techniques are also used in immunohistochemistry and western blotting for diagnosis, and in antigen and enzyme assays such as, for example, ELISA and other diagnostic immunoassays.

The unique fluorescent spectrum of the compounds, as exemplified in FIGS. 1 and 2, makes them useful alone in any of the above-described techniques or in combination with other fluorescent compounds allowing for multicolor analysis in any of the above-described techniques.

The following nonlimiting examples are provided to further illustrate the present invention.

EXAMPLES

Example 1

Preparation of Starting Materials

The mercaptoaminotriazoles (Formula I) employed herein were prepared as described in Reid and Heindel (Journal of Heterocyclic Chemistry 1976 13:925–926). Specifically, 4-amino-3-(2-pyridyl)-5-mercapto[4H]-1,2,4-triazole (Formula I wherein R is 2-pyridyl; mp 190–191° C.) and 4-amino-3-(3-pyridyl)-5-mercapto[4H]-1,2,4-triazole (Formula I wherein R is 3-pyridyl; mp=192–193° C.) were prepared and characterized in accordance with the procedure of Reid and Heindel (Journal of Heterocyclic Chemistry 1976 13:925–926). Melting points were obtained in capillaries in a MelTemp apparatus and are reported uncorrected. NMR analyses were performed in the solvents indicated on a Bruker 360 MHz NMR spectrometer. All solvents and reagents employed were of the highest commercially available purities.

Example 2

One-Step Synthesis of Compound IIa

To prepare Compound IIa by one-step preparation, 102 mg (0.53 mmol) of 4-amino-3-(4-pyridyl)-5-mercapto[4H]-1,2,4-triazole were refluxed with 740 µL (0.53 mmol) of triethylamine in 25 mL of anhydrous ethanol until complete dissolution. To this solution was added α-bromocinnamaldehyde (197 mg, 0.93 mmol) and the mixture was refluxed for 5 hours. Over time the product precipitated out of solution and, after cooling down the reaction to room temperature, it was isolated by filtration and washed with ethanol. Yellow crystals were obtained after recrystallization from ethanol/DMSO. 92 mg, 57%, mp=245–246° C. Anal. Calcd. for $C_{16}H_{11}N_5S$: C, 62.93%; H, 3.63%; N, 22.93%. Found: C, 62.86%; H, 3.42%; N, 22.86%. $^1H$ NMR ($d_6$-DMSO) δ: 7.47–7.63 (m, 6H, Ph and $H_y$); 7.99 (dd, J=1.5 Hz, J'=4.5 Hz, 2H, $H_b$); 8.23 (s, 1H, $H_α$); 8.77 (dd, J=1.5 Hz, J'=4.5 Hz, 2H, $H_a$).

Example 3

One-Step Synthesis of Compound IIb

To prepare Compound IIb by one-step preparation, 105 mg (0.54 mmol) of 4-amino-3-(2-pyridyl)-5-mercapto[4H]-1,2,4-triazole were refluxed with 760 µL (0.54 mmol) of triethylamine in 25 mL of anhydrous ethanol until complete dissolution. To this solution was added α-bromocinnamaldehyde (202 mg, 0.96 mmol) and the mixture was refluxed for 5 hours. Over time the product precipitated out of solution and, after cooling down the reaction to room temperature, it was isolated by filtration and washed with ethanol. Yellow crystals were obtained after recrystallization from ethanol/DMSO. 91 mg, 55%, mp=205–207° C. Anal. Calcd. for $C_{16}H_{11}N_5S$: C, 62.93%; H, 3.63%; N, 22.93%. Found: C, 62.43%; H, 3.32%; N, 22.71%. $^1H$ NMR ($d_6$-DMSO) δ: 7.47–7.64 (m, 7H, Ph, $H_c$, $H_y$); 7.93–7.96 (m, 1H, $H_d$); 7.99–8.04 (m, 1H, $H_b$); 8.17 (s, 1H, $H_α$); 8.76–8.78 (m, 1H, $H_a$).

Example 4

One-Step Synthesis of Compound IIc

To prepare Compound IIc by one-step preparation, 110 mg (0.57 mmol) of 4-amino-3-(3-pyridyl)-5-mercapto[4H]-1,2,4-triazole were refluxed with 800 µL (0.57 mmol) of triethylamine in 25 mL of anhydrous ethanol until complete dissolution. To this solution was added α-bromocinnamaldehyde (212 mg, 1.00 mmol) and the mixture was refluxed for 5 hours. Overtime the product precipitated out of solution and, after cooling down the reaction to room temperature, it was isolated by filtration and washed with ethanol. Yellow crystals were obtained after recrystallization from ethanol/DMSO. 104 mg, 60%, mp=228–229° C. Anal. Calcd. for $C_{16}H_{11}N_5S+0.8H_2O$: C, 60.10%; H, 3.97%; N, 21.90%. Found: C, 60.01%; H, 3.61%; N, 21.40%. $^1H$ NMR ($d_6$-DMSO) δ: 7.48–7.64 (m, 7H, Ph, $H_d$, $H_y$); 8.20 (s, 1H, $H_α$); 8.31–8.36 (m, 1H, $H_c$); 8.72–8.75 (m, 1H, $H_b$); 9.12 (s, 1H, $H_a$).

Example 5

Two-Step Synthesis of Compound IId

To prepare Compound IId by a two-step synthetic process one must first prepare (step I) the imine from the condensation of the mercaptoaminotriazole of Formula I [in this case the 5-(2-thienyl)-analog] and α-bromocinnamaldehyde. The methodology is set forth in WO 00/10564 which is herein incorporated by reference in its entirety. Thereafter, (step II), 100 mg (0.26 mmol) of this 4-imino-α-bromocinnamyl)-3-mercapto-5-(2-thienyl)-4H-1,2,4-triazole were refluxed with 83 µL (1.02 mmol) of pyridine in 35 mL of anhydrous ethanol until no more of the starting triazole could be detected by thin layer chromatography (hexanes 70%/ethyl acetate 30%). The reaction mixture was evaporated to dryness and the residue obtained purified by flash silica gel column chromatography (hexanes 70%/ethyl acetate 30%) leading to the isolation of a yellow solid as the final product. 32 mg, 40%, mp=180–183° C. Anal. Calcd. for $C_{15}H_{10}N_4S_2+0.2H_2O$: C, 57.38%; H, 3.34%; N, 17.84%. Found: C, 57.66%; H, 3.35%; N, 17.20%. $^1H$ NMR ($d_4$-MeOH) δ: 7.22 (dd, J=3.7 Hz, J'=5.0 Hz, 1H, $H_b$); 7.38–7.64 (m, 6H, Ph and $H_y$); 7.70 (dd, J=1.2 Hz, J'=5.0 Hz, 1H, $H_c$); 8.01 (dd, J=1.2 Hz, J'=3.7 Hz, 2H, $H_a$); 8.04 (s, 1H, $H_α$).

Example 6

One-Step Synthesis of Compound IId

To prepare compound IId by a one-step synthetic process, 117 mg (0.59 mmol) of 4-amino-3-(2-thienyl)-5-mercapto[4H]-1,2,4-triazole were refluxed with 83 µL (0.59 mmol) of triethylamine in 10 mL of anhydrous ethanol. To this solution was added α-bromocinnamaldehyde (218 mg, 1.03 mmol) and the mixture was refluxed until no more of the starting triazole could be detected by thin layer chromatography (hexanes 70%/ethyl acetate 30%). Over time the product precipitated out of solution and, after cooling down the reaction to room temperature, it was isolated by filtration and washed with ethanol. Yellow crystals were obtained, 129 mg (70%). Same physical characteristics as IId isolated through the two-step process.

Example 7

One-Step Synthesis of Compound IIe

To prepare compound IIe by a one-step synthetic process, 100 mg (0.55 mmol) of 4-amino-3-(2-furyl)-5-mercapto[4H]-1,2,4-triazole were refluxed with 76 µL (0.55 mmol) of triethylamine in 10 mL of anhydrous ethanol. To this solution was added α-bromocinnamaldehyde (203 mg, 0.96 mmol) and the mixture was reluxed until no more of the starting triazole could be detected by thin layer chromatography (hexanes 70%/ethyl acetate 30%). Over time the product precipitated out of solution and, after cooling down the reaction to room temperature, it was isolated by filtration and washed with ethanol. Yellow crystals were obtained, 125 mg (77%). $^1H$ NMR ($d_6$-DMSO) δ: 6.74 (dd, J=3.5 Hz, J'=2.0 Hz, 1H, $H_b$); 7.23 (dd, J=1.0 Hz, J'=3.5 Hz, 1H, $H_c$); 7.46–7.62 (m, 6H, Ph and $H_y$); 7.98 (dd, J=1.0 Hz, J'=2.0 Hz, 2H, $H_a$) 8.20 (d, J=0.5 Hz, 1H, $H_α$).

Example 8

One-Step Synthesis of Compound IIf

To prepare compound IIf by a one-step synthetic process, 103 mg (0.47 mmol) of 4-amino-3-{1-(2-phenyl)-ethyl}-5-mercapto[4H]-1,2,4-triazole were refluxed with 65 μL (0.47 mmol) of triethylamine in 10 mL of anhydrous ethanol. To this solution was added α-bromocinnamaldehyde (212 mg, 1.00 mmol) and the mixture was refluxed until no more of the starting triazole could be detected by thin layer chromatography (hexanes 70%/ethyl acetate 30%). Over time the product precipitated out of solution and, after cooling the reaction to room temperature, it was isolated by filtration and washed with ethanol. Pale yellow crystals were obtained, 98 mg (63%). Anal. Calcd. for $C_{19}H_{16}N_4S$: N, 16.85%. Found: N, 16.64%. $^1$H NMR (d$_6$-DMSO) δ: 3.03 (t, J=7.8 Hz, H$_b$); 3.12 (t, J=7.8 Hz, H$_a$); 7.19–7.30 (m, 5H, Ph) 7.45–7.60 (m, 6H, Ph and H$_\gamma$); 8.10 (d, J=1.0 Hz, 1H, H$_\alpha$).

Example 9

One-Step Synthesis of Compound IIg

To prepare compound IIg by a one-step synthetic process, 107 mg, (0.52 mmol) of 4-amino-3-(3-methoxyphenyl)-5-mercapto[4H]-1,2,4-triazole were refluxed with 72 μL (0.52 mmol) of triethylamine in 10 mL of anhydrous ethanol. To this solution was added α-bromocinnamaldehyde (167 mg, 0.79 mmol) and the mixture was refluxed until no more of the starting triazole could be detected by thin layer chromatography (chloroform 95%/methanol 5%). Over time the product precipitated out of solution and, after cooling the reaction to room temperature, it was isolated by filtration and washed with ethanol. tanned crystals were obtained after recrystallisation from acetone, 121 mg (70%), mp=202–203° C. Anal. Calcd. for $C_{15}H_{10}N_4S_2+0.25H_2O$: C, 63.79%; H, 4.31%; N, 16.53%. Found: C, 63.84%; H, 4.22%; N, 16.41%. $^1$H NMR (d$_6$-DMSO) δ: 3.82 (s, 3H, CH$_3$); 7.11–7.15 (m, 1H, H$_b$); 7.47–7.62 (m, 9H, Ph and H$_{a/b/c/\gamma}$); 8.19 (s, 1H, H$_\alpha$).

Example 10

One-Step Synthesis of Compound IIh

To prepare compound IIh by a one-step synthetic process, 124 mg, (0.48 mmol) of 4-amino-3-(4-trifluoromethylphenyl)-5-mercapto[4H]-1,2,4-triazole were refluxed with 66 μL (0.48 mmol) of triethylamine in 10 mL of anhydrous ethanol. To this solution was added α-bromocinnamaldehyde (150 mg, 0.71 mmol) and the mixture was refluxed until no more of the starting triazole could be detected by thin layer chromatography (chloroform 95%/methanol 5%). Over time the product precipitated out of solution and, after cooling the reaction to room temperature, it was isolated by filtration and washed with ethanol. Yellow crystals were obtained after recrystallisation from acetone, 125 mg (70%), mp=246–247° C. Anal. Calcd. for $C_{15}H_{10}N_4S_2+0.5H_2O$: C, 56.69%; H, 3.17%; N, 14.69%. Found: C, 56.87%; H, 2.88%; N, 14.48%. $^1$H NMR (d$_6$-DMSO) δ: 7.47–7.64 (m, 6H, Ph and H$_\gamma$); 7.94 (d, J=8.4 Hz, 2H, H$_b$); 8.23 (s, 1H, H$_\alpha$); 8.24 (d, J=8.4 Hz, 2H, H$_a$).

Example 11

One-Step Synthesis of Compound IIi

To prepare compound IIi by a one-step synthetic process, 152 mg (0.72 mmol) of 4-amino-3-(4-fluoromethylphenyl)-5-mercapto[4H]-1,2,4-triazole were refluxed with 100 μL (0.72 mmol) of triethylamine in 10 mL of anhydrous ethanol. To this solution was added α-bromocinnamaldehyde (267 mg, 1.27 mmol) and the mixture was refluxed until no more of the starting triazole could be detected by thin layer chromatography (chloroform 95%/methanol 5%). Over time the product precipitated out of solution and, after cooling the reaction to room temperature, it was isolated by filtration and washed with ethanol. Orange crystals were obtained after recrystallisation from acetone, 105 mg (45%), mp=254–255° C. $^1$H NMR (d$_6$-DMSO) δ: 7.40–7.64 (m, 8H, Ph and H$_{b/\gamma}$); 8.03–8.07 (m, 2H, H$_a$); 8.19 (s, 1H, H$_\alpha$).

What is claimed is:

1. A compound of Formula II,

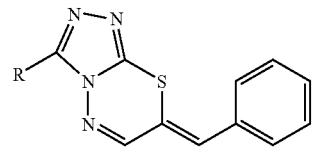

wherein R is selected from the group consisting of a furyl, a thienyl, a pyridyl, an alkyl, an aryl or arylalkyl, a 1-(2-phenyl)-ethyl, a 3-methoxyphenyl, a 4-trifluoromethylphenyl and 4-fluorophenyl group.

2. The compound of claim 1 wherein the pyridyl is selected from the group consisting of 2-pyridyl, 3-pyridyl and 4-pyridyl.

3. The compound of claim 1 selected from the group consisting of:

compound IIa, compound IIb compound IIc,

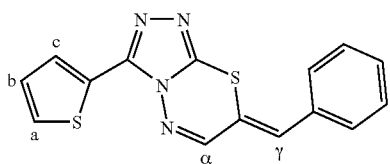

compound IId,

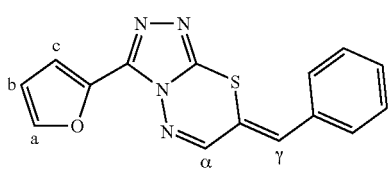

compound IIe,

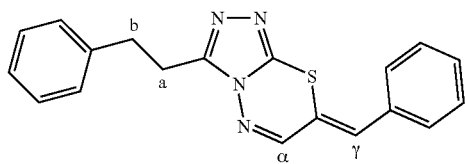

compound IIf,

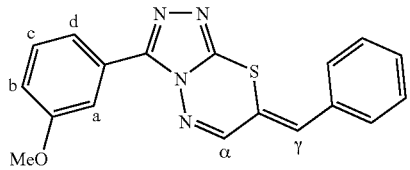

compound IIg,

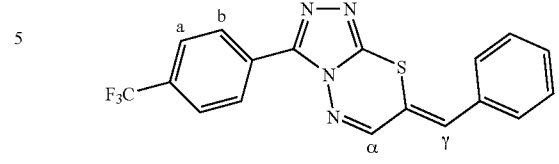

compound IIh, and

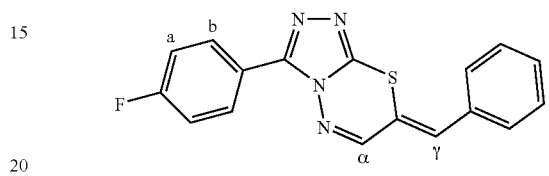

compound IIi.

4. A one step method for synthesizing the compound of claim 1 comprising adding an α-halocinnamaldehyde to a solution comprising a mercaptoaminotriazole and a tertiary amine and precipitating the compound of Formula II therefrom.

5. A two step method for synthesizing the compound of claim 1 comprising:
(a) deriving a bromocinnamyl imine from condensation of a mercaptoaminotriazole with α-bromocinnamaldehyde; and
(b) refluxing this bromocinnamyl imine with a tertiary amine to produce the compound of Formula II.

6. The method of claim 5 wherein a bromocinnamyl imine is refluxed with triethylamine or pyridine in solvent or with the tertiary amine itself as solvent to effect a ring closure to compounds of Formula II.

7. A pharmaceutical composition comprising the compound of claim 1 and a pharmaceutically acceptable vehicle.

8. A method for inhibiting a bacterial infection in an animal comprising administering to the animal the pharmaceutical composition of claim 7.

* * * * *